United States Patent
Nudelman

[11] 3,956,291
[45] May 11, 1976

[54] 7-THIOACETAMIDO CEPHALOSPORANIC ACID DERIVATIVES

[75] Inventor: Abraham Nudelman, Bala Cynwyd, Pa.

[73] Assignee: American Home Products Corporation, New York, N.Y.

[22] Filed: Nov. 8, 1974

[21] Appl. No.: 522,362

[52] U.S. Cl. .................. 260/243 C; 260/453 R; 260/455 R; 260/465 G; 260/465.7; 260/465.9; 424/246
[51] Int. Cl.$^2$................................ C07D 501/28
[58] Field of Search .......................... 260/243 C

[56] References Cited
UNITED STATES PATENTS

| | | | |
|---|---|---|---|
| 3,875,153 | 4/1975 | Treuner et al. | 260/243 C |
| 3,892,735 | 7/1975 | Treuner et al. | 260/243 C |

Primary Examiner—Alton D. Rollins
Assistant Examiner—Diana G. Rivers
Attorney, Agent, or Firm—Richard K. Jackson

[57] ABSTRACT

The compounds of the following formula are antibacterial agents:

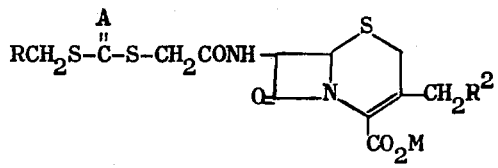

in which
R is —H, —CN, carbo(lower)alkoxy, phenyl, halophenyl, nitrophenyl, carboxy, —C CH, or —CH=CH$_2$;
R$^2$ is —H, lower alkanoyloxy or, when M is —H, N-pyridinium;
M is —H, an alkali metal, an alkaline earth metal or the ammonium ion;
and
A is =NCN, =NSO$_2$CH$_3$, =CHNO$_2$ or

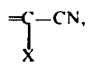

wherein X is —CN, —CONH$_2$, phenyl or —SO$_2$CH$_3$.

1 Claim, No Drawings

7-THIOACETAMIDO CEPHALOSPORANIC ACID DERIVATIVES

DESCRIPTION OF THE INVENTION

In accordance with this invention, there is provided a group of antibacterial compounds of the formula:

$$RCH_2S-\overset{A}{\underset{\|}{C}}-S-CH_2COHN-\left[\text{cephem ring with } CH_2R^2, CO_2M\right]$$

in which

R is —H, CN, carbo(lower)alkoxy, phenyl, halophenyl, nitrophenyl, carboxy, —C≡CH, —CH=CH$_2$;

R$^2$ is —H, lower alkanoyloxy or, when M is —H, N-pyridinium;

M is —H, an alkali metal, an alkaline earth metal or the amonium ion; and

A is =NCN, =NSO$_2$CH$_3$, =CHNO$_2$ or $$=\underset{X}{\overset{}{C}}-CN,$$

wherein X is —CN, —CONH$_2$, phenyl or —SO$_2$CH$_3$.

The carbo(lower)alkoxy group represented by R may contain from 1 to 6 carbon atoms in the alkoxy moiety. The lower alkanoxyloxy groups represented by R$^2$ may be acetoxy, propionyloxy, butanoyloxy or amyloxy, the acetoxy group being preferred.

The compounds of this invention are useful for the treatment of bacterial infections amenable to treatment by cephalosporins. They effectively inhibit the growth of gram-positive, gram-negative and penicillin resistant bacterial strains as are more specifically detailed in the examples. The activity of the compounds of this invention was established in accordance with the well known, scientifically recognized agar serial dilution test procedure whereby the minimum inhibitory concentration of a specific antibacterial agent required to completely inhibit the growth of a given bacterium is established. In accordance with the results obtained with the antibacterial compounds of this invention, their usefulness is established in the fields of comparative pharmacology and microbiology for the purpose of inhibiting the growth of undesirable bacterial colonies.

The compounds of this invention are prepared by reacting a compound of the formula:

$$A=\underset{\underset{SM}{|}}{\overset{\overset{SCH_2R}{|}}{C}}$$

in which A and R are defined above and M is an alkali metal, especially sodium or potassium, with 7-bromoacetamido cephalosporanic acid. The product is readily converted to an alkali metal, alkaline earth metal or ammonium salt by treatment with the corresponding base under mild conditions. Sodium or potassium 2-ethylhexanoate provide a convenient reagent for neutralization to the alkali metal salts of the cephalosporanic acids of this invention.

The reactants:

$$A=\underset{\underset{SM}{|}}{\overset{\overset{SCH_2R}{|}}{C}}$$

as defined above, are generally known in the chemical literature. The specific reactants employed in the production of the compounds of this invention are produced by the methods used for the production of the known compounds. Exemplary of the literature references, exclusive of those specifically cited in the following examples, are:

Jensen et al., *Acta. Chem. Scand.*, 22,1107(1968)
Davis et al., *J. Chem. Soc.* (C)124(1967)
Yokoyama, *Bull. Chem. Soc. Japan*, 43,2938(1970)
Freund, *Ber.* 52,542(1919)
Matthews et al. *J. Org. Chem.* 25,266(1960) and
Brownstein, *J. Org. Chem.* 23,113(1958).

The nmr spectra described in the following examples pertains to the spectra obtained upon exchanging acidic hydrogens with deuterium and are described in ppm. ($\delta$). The small amount of water and/or solvent carried into the products is readily removed by gently heating the material under vacuum. The biological activity data presented after each example illustrates the activity of the product against specific bacterium of the designated strain in terms of the minimum inhibitory concentration in micrograms per milliliter needed to completely inhibit growth of the test organism. The abbreviations used are:

BA SU — *Bacillus subtilis*
St AU — *Staphylococcus aureus*
NE CA — *Neisseria catarrhalis*
ES CO — *Escherichia coli*
SA PA — *Salmonella paratyphi*
KL PN — *Klebsiella pneumoniae*
BO BR — *Bordetella brochiseptica*
PR VU — *Proteus vulgaris*
HE SP — *Herellea species*
EN SE — *Enterobacter aerogenes*
PS AE — *Pseudomones aeruginosa*
ES IN — *Escherichia intermedia*

EXAMPLE 1

7-(2[2,2-Dicyano-1-(ethoxycarbonylmethylthio)ethenylthio]acetamido)cephalosporanic acid Suspend malononitrile (6.6 g, 0.1 moles) and powdered potassium hydroxide (13.2 g, 0.2 moles, 85% pure) in 100 ml of dry dioxane. The mixture is cooled to 10°C and a solution of carbon disulfide (7.6 g, 6 ml, 0.1 moles) in 10 ml of dioxane is added. The mixture is stirred for 1 hour. A yellow precipitate collects on the walls which is dislodged upon addition of 75 ml of water. The solution thus obtained is cooled to 5°C and ethyl bromoacetate (16.7 g, 11.02 ml, 0.1 moles) is added. After stirring for one hour the solution is acidified with 6 ml of concentrated hydrochloric acid, and is flash concentrated to 10 ml at 20°C. The residue is extracted with ethyl acetate and saturated sodium chloride. The organic phase is dried, flash concentrated and added to 800 ml of diethyl ether-dichloromethane (1:1 ratio). The yellow product obtained is [(2,2-dicyano- 1-mercaptovinyl)thio] acetic acid ethyl ester, sodium salt, 4.4 g (17.5% yield), mp. 230°–232°C. nmr (DMSO-D$_6$) 1.20 (t, 3), 4.10 (q, 2), 4.13 (s, 2)

Elemental Analysis for C$_8$H$_7$N$_2$NaO$_2$S$_2$: Calc'd: C, 38.39; H, 2.82; N, 11.20. Found: C, 38.14; H, 2.89; N, 11.08.

To a solution of [(2,2-dicyano-1-mercaptovinyl)thio] acetic acid ethyl ester sodium salt (1.0 g, 0.04 moles) and 7-bromoacetamidocephalosporanic acid (1.57 g, 0.04 moles) in 150 ml of acetone is added 200 mg of potassium iodide and the mixture is stirred at room temperature for 18 hours, filtered and the filtrate flash evaporated. The residue is dissolved in a mixture of water and ethyl acetate. The organic phase is dried, flash concentrated to 10 ml and added to pentane. The precipitated solid (1.75 g, 77% yield) is filtered and dried to yield the title compound, nmr (DMSO-D$_6$) 1.25 (t, 3), 2.02 (s, 3), 3.58 (broad s, 2), 3.97–4.42 (superimposed q, 2 at 4.15, s, 2, at 4.19 and s, 2 at 4.29), 4.90 (q, 2), 5.16 (d, 1), 5.70 (d, 1).

Elemental Analysis for C$_{20}$H$_{20}$N$_4$O$_8$S$_3$.1.5 H$_2$O: Calc'd: C, 42,32; H, 4.08; N, 9.87. Found: C, 41.96; H, 3.64; N, 9.65.

| Bacterium | Strain | Minimum Inhibitory Concentration micrograms per millititer |
|---|---|---|
| BA SU | 6633 | .244 |
| ST AU | 6538P | .976 |
| " | Smith | .976 |
| " | CHP | 7.81 |
| " | 53–180 | 3.90 |
| NE CA | 8193 | 125 |
| ES CO | 9637 | 250 |
| SA PA | 11737 | 125 |
| KL PN | 10031 | 250 |
| BO BR | 4617 | 250 |
| PR VU | 6896 | 125 |

EXAMPLE 2

7-(2-[2,2-Dicyano-1-(cyanomethylthio)ethenylthio]acetamido)cephalosporanic acid

Following the procedure presented in the first paragraph of Example 1, 2-(cyanomethylthio)-2-mercapto-1,1-vinyldicarbonitrile potassium salt is prepared in 71.4% yield from di(potassium mercapto)methylene malononitrile, m.p. 300°C. (decomp.), nmr (DMSO-D$_6$) 3.33(s).

Elemental Analysis for C$_6$H$_2$KN$_3$S$_2$.H$_2$O: Calc'd: C, 30.36; H, 1.70; N, 17.70. Found: C, 30.77; H, 1.66; N, 17.79.

The following the procedure disclosed in the second paragraph of Example 1, the title compound is prepared in 32 percent yield from 2-(cyanomethylthio)-2-mercapto-1,1-vinyldicarbonitrile potassium salt prepared in the preceding paragraph, nmr (DMSO-D$_6$) 2.10 (s, 3), 3.68 (broad s, 2), 4.33 (s, 2), 4.54 (s, 2), 4.96 (q 2), 5.32 (d, 1), 5.80 (d, 1).

Elemental Analysis for C$_{18}$H$_{15}$N$_5$S$_3$O$_6$.2H$_2$0.1/2CH$_3$CO$_2$CH$_2$CH$_3$: Calc'd: C, 41.31; H, 3.84; N, 12.70. Found: C, 41.34; H, 3.15; N, 12.39.

The potassium salt of the title compound is prepared by reaction of the free acid with an equimolar amount of potassium 2-ethyl hexanoate in ethyl acetate. The potassium salt of 7-(2[2,2-dicyano-1-(cyanomethylthio)vinylthio]acetamido)cephalosporanic acid is recovered by diluting the ethyl acetate solution with diethyl ether, filtering and washing the product with diethyl ether.

Elemental Analysis for C$_{18}$H$_{14}$KN$_5$O$_6$S$_3$.2H$_2$O: Calc'd: C, 38.08; H, 3.20; N, 12.34. Found: C, 38.33; H, 2.82; N, 11.53.

| BA SA | 6633 | .061 |
|---|---|---|
| ST AU | 6538P | .488 |
| " | Smith | .488 |
| " | CHP | 1.95 |
| " | 53–180 | 1.95 |
| NE CA | 8193 | 15.6 |
| SA PA | 11737 | 15.6 |
| ES CO | 9637 | 31.3 |
| KL PN | 10031 | 15.6 |
| BO BR | 4617 | 62.5 |
| PR VU | 6896 | 31.3 |
| HE SP | 9955 | 250 |
| ES CO | 920 | 250 |

EXAMPLE 3

7-(2-[2-Carbamoyl-1-(methoxycarbonylmethylthio)-2-cyanoethenylthio]acetamido) cephalosporanic acid A solution of [(2-carbamoyl-2-cyano-1-mercaptovinyl)thio]acetic acid methyl ester (produced by the method of Gompper et al., Ber. 95,2861(1962) (246 mg, 1 mmole), diisopropylethylamine (129 mg, 1 mmole) and 7-bromoacetamido cephalosporanic acid (393 mg, 1 mmole) in 10 ml of acetone is stirred at room temperature for 17 hours. The solution is flash evaporated, the residue is dissolved in 15 ml of water covered with 50 ml of ethyl acetate, and acidified with 6N hydrochloric acid to pH 1.5. The organic phase is separated, dried, flash concentrated to 5 ml and added to pentane. The precipitated solid (150 mg, 27% yield) is filtered and dried, nmr (DMSO-D$_6$) 1.07 (s, 3), 3.64 (broad s, 2), 3.70 (s, 3), 4.01 (s, 2), 4.14 (s, 2), 4.93 (q, 2 ) 5.20 (d, 1), 5.86 (d, 1).

Elemental Analysis for C$_{19}$H$_{20}$N$_4$O$_9$S$_3$.H$_2$O: Calc'd: C, 40.56; H, 3.94; N, 9.96. Found: C, 40.35; H, 3.86; N, 9.78.

| BA SU | 6633 | .122 |
|---|---|---|
| ST AU | 6538P | .488 |
| " | Smith | .488 |
| " | CHP | 3.90 |
| " | 53–180 | 1.95 |
| NE CA | 8193 | 7.81 |
| ES CO | 9637 | 62.5 |
| SA PA | 11737 | 31.3 |
| KL PN | 10031 | 125 |
| PR VU | 6896 | 62.5 |

EXAMPLE 4

7-(2-[2-Carbamoyl-2-cyano-1-(ethoxycarbonylmethylthio)ethenylthio)]acetamido)cephalosporanic acid The title compound is prepared under the conditions described in Example 3 using [(2-carbamoyl-22-cyano-1-mercaptovinyl)thio]acetic acid ethyl ester; [prepared by the method of Yokoyama, Bull. Chem. Soc. Japan, 44,1610(1971)] and replacing the acetone for acetonitrile as solvent. The product is obtained in 56% yield, nmr (DMSO-D$_6$) 1.28 (t, 3), 2.05 (s, 3), 3.60 (broad s, 2), 3.97 (s, 2), 4.26 (q, 2), 4.92 (q, 2), 5.19 (d, 1), 5.77 (d, 1).

Elemental Analysis for C$_{20}$H$_{22}$N$_4$O$_9$S$_3$.1/2H$_2$O: Calc'd: C, 42.32; H, 4.09; N, 9.87. Found: C, 42.59; H, 4.03; N, 9.25.

| | | |
|---|---|---|
| BA SU | 6633 | .061 |
| ST AU | 6538P | .488 |
| " | Smith | .488 |
| " | CHP | 3.90 |
| " | 53-180 | 1.95 |
| NE CA | 8193 | 3.90 |
| ES CO | 9637 | 250 |
| SA PA | 11737 | 62.5 |
| KL PN | 10031 | 125 |
| PR VU | 6896 | 125 |

EXAMPLE 5

7-[2-[cyanoimino)(methylthio)methylthio]acetamido]cephalosporanic acid

The title compound is prepared in 45% yield by the same procedure and in the same molar amounts as described in Example 1 from potassium methyl cyanodithioimidocarbonate prepared by the method of Timmons et al. *J. Org. Chem.* 32,1566(1967), nmr (DMSO-$D_6$) 2.04 ($s$, 3), 2.72 ($s$, 3), 3.58 (broad $s$, 2) 4.17 ($s$, 2), 4.86 ($q$, 2) 5.15 ($d$, 1), 5.73 ($d$, 1).

Elemental Analysis for $C_{15}H_{16}N_4O_6S_3$: Calc'd: C, 40.53; H, 3.63; N, 12.60. Found : C, 40.40; H, 3.79; N, 12.09.

| | | |
|---|---|---|
| BA SU | 6633 | .976 |
| ST AU | 6538P | 1.95 |
| " | Smith | .976 |
| " | CHP | 7.81 |
| " | 9637 | 125 |
| " | 53-180 | 3.90 |
| NE CA | 8193 | 250 |
| SA PA | 11737 | 31.3 |
| KL PN | 10031 | 125 |
| BO BR | 4617 | 125 |
| PR VU | 6896 | 62.5 |
| ES CO | 920 | 250 |

EXAMPLE 6

7-[2-(1-Cyanomethylthio-2-nitroethenylthio)acetamido]cephalosporanic acid

To a solution of nitro-dithioacetic acid dipotassium salt [prepared by the method of Freund, Ber., 52,542(1919)] (4.26 g, 0.02 moles) in 50 ml of acetone and 30 ml of water is added a solution of chloroacetonitrile (1.64 g. 0.02 moles) in 5 ml of acetone. The solution is stirred at room temperature for one hour and is then flash evaporated to dryness. The obtained residue is stirred with 100 ml of acetone and filtered. The filtrate is concentrated to 25 ml and the product (2.65 g, 62% yield) is crystallized upon addition of diethyl ether to yield (1-mercapto-2-nitrovinylthio)acetonitrile potassium salt, mp. 151°–153°C., nmr (DMSO-$D_6$), 4.20 ($s$, 2), 7.57 ($s$, 1). Elemental Analysis for $C_4H_3KN_2O_2S_2$: Calc'd: C, 22.42; H, 1.41; N, 13.07. Found : C, 23.25; H, 1.66; N, 12.99.

The title compound is prepared in 60% yield by the same procedure and in the same molar amounts as described in Example 1 from (1-mercapto-2-nitrovinylthio)acetonitrile potassium salt, nmr (DMSO-$D_6$) 1.07 ($s$, 3), 1.61 (broad $s$, 2), 4.23 ($s$, 2), 4.43 ($s$, 2), 4.92 ($q$, 2), 5.17 ($d$, 1), 5.80 ($d$, 1).

Elemental Analysis for $C_{16}H_{16}N_4O_8S_3 \cdot H_2O$.

Calc'd: C, 37.94; H, 3.58; N, 11.07. Found : C, 37.97; H, 3.36; N, 10.73.

To a solution of the product of the preceding paragraph (867 mg, 1.71 mmoles) in 25 ml of ethylacetate, a solution of potassium 2-ethylhexanoate (2M, 0.857 ml, 1.71 mmoles) is added under vigorous stirring. The mixture is diluted with diethyl ether, filtered, washed repeatedly with diethyl ether and dried, the product is obtained in 87% yield.

Elemental Analysis for $C_{16}H_{15}KN_4O_8S_3 \cdot H_2O$: Calc'd: C, 35.28; H, 3.15; N, 10.29. Found : C, 35.42; H, 2.96; N, 9.55.

| | | |
|---|---|---|
| BA SU | 6633 | .122 |
| ST AU | 653P | .976 |
| " | Smith | .976 |
| " | CH | 3.90 |
| " | 53-180 | 3.90 |
| NE CA | 8193 | 62.5 |
| PS AE | 10145 | 250 |
| EX CO | 9637 | 62.5 |
| ES IN | 65-1 | 250 |
| SA PA | 11737 | 7.81 |
| KL PN | 10031 | 62.5 |
| BO BR | 4617 | 125 |
| PR VU | 6896 | 31.3 |
| HE SP | 9955 | 125 |
| ES CO | 920 | 125 |

EXAMPLE 7

7-[2-[(cyanoimino)(cyanomethylthio)methylthio]acetamido]cephalosporanic acid

The title compound is prepared in 64% yield by the same procedure and in the same molar amounts as described in Example 1 from potassium cyanomethyl cyanoimidodithiocarbonate (produced by the method of Timmons, U.S. Pat. No. 3,658,901) nmr (DMSO-$D_6$) 2.05 ($s$, 3), 3.60 (broad $s$, 2), 4.38 ($s$, 2), 4.52 ($s$, 2), 4.91 ($q$, 2), 5.19 ($d$, 1) 4.78 ($d$, 1).

Elemental Analysis for $C_{16}H_{15}N_5O_6S_3 \cdot H_2O$: Calc'd : C, 39.41; H, 3.52; N, 14.37. Found : C, 39.43; H, 3.30; N, 12.55.

The potassium salt of the title compound is prepared in 69% yield by the same procedure as described in Example 6 from the product of Example 7.

Elemental Analysis for $C_{16}H_{14}KN_5O_6S_3 \cdot 2H_2O$: Calc'd : C, 35.35; H, 3.34; N, 12.88. Found : C, 35.01; H, 2.84; N, 11.68.

| | | |
|---|---|---|
| BA SU | 6633 | .061 |
| ST AU | 6538P | .488 |
| " | Smith | .488 |
| " | CHP | 195 |
| " | 53-180 | .976 |
| NE CA | 8193 | 31.3 |
| ES CO | 9637 | 31.3 |
| ES IN | 65-1 | 62.5 |
| EN AE | 13048 | 7.81 |
| BO BR | 4617 | 15.6 |
| PR VU | 6896 | 31.3 |
| HE SP | 9955 | 31.3 |

EXAMPLE 8

7-(2-[2-Cyano-1-(cyanomethylthio)-2-phenylethenylthio]acetamido)cephalosporanic acid To a solution of cyanophenyldithioacetic acid disodium salt (prepared by the method of Davis et. al., J. Chem. Soc. (C) 124(1967) in aqueous acetone is added an equimolar amount of chloroacetonitrile in acetone. The solution is stirred at room temperature for one hour and taken to dryness. The residue is stirred with 100 ml. of acetone and filtered. The filtrate is concentrated to 25 ml. and the product is crystallized upon addition of diethyl ether. Recrystallization from dichloromethane gives (2-cyano-1-mercapto-2-phenyl-vinylthio)acetonitrile sodium salt m.p. 205°–207°C., the nmr spectrum indicates the product is a mixture of cis and trans isomers, nmr (DMSO-$D_6$) 4.40 (s), 4.48 (s), 7.1–7.6 (m), 8.0–8.4 (m).

Elemental Analysis for $C_{11}H_7N_2NaS_2$: Calc'd: C, 51.95; H, 2.77; N, 11.02. Found : C, 51.65; H, 2.85; N, 10.84.

The title compound is prepared in 77% yield, by the same procedure and in the same molar amounts as described in Example 1, from the compound produced in the preceding paragraph. The nmr spectrum indicated that the product consists of an approximately equal mixture of cis and trans isomers, 2.03 (s, 3), 3.59 (broad s, 2), 3.80 and 3.97 (two s, total area 2), 4.10 and 4.25 (two s, total area 2), 4.90 (q, 2) 5.15 (d, 1), 5.73 (d, 1) 7.53 and 7.58 (two s, total area 5).

Elemental Analysis for $C_{23}H_{20}N_4O_6S_3 \cdot 1/2H_2O$: Calc'd : C, 48.98; H, 3.82; N, 10.12. Found : C, 49.79; H, 3.68; N, 10.00.

The potassium salt of the title compound is prepared in 79% yield by the same procedure as described in Example 1.

Elemental Analysis for $C_{23}H_{19}KN_4O_6S_3 \cdot H_2O$. Calc'd : C, 45.98; H, 3.52; N, 9.32. Found : C, 45.95; H, 3.17; N, 9.16.

| BA SU | 6633 | .031 |
|---|---|---|
| ST AU | 6538P | .244 |
| " | Smith | .244 |
| " | CHP | .976 |
| " | 53–180 | .976 |
| NR CA | 8193 | 3.90 |
| SA PA | 11737 | 62.5 |
| KL PN | 10031 | 62.5 |
| BO BR | 4617 | 250 |
| PR VU | 6896 | 250 |
| ES CO | 920 | 250 |
| ES CO | 9637 | 25 |

EXAMPLE 9

7-[2-(1-Benzylthio-2-nitroethenylthio)acetamido]-cephalosporanic acid

Following the procedure presented in the first paragraph of Example 6, 1-(benzylthio)-2-nitroethenethiol potassium salt is prepared in 47% yield from nitrodithioacetic acid dipotassium salt and benzyl bromide, m.p. 196°–198°C., (decomp.), nmr (DMSO-$D_6$) 4.40 (s, 2), 7.30 (s, 5), 7.54 (s, 1)

Elemental Analysis for $C_9H_8NS_2O_2K \cdot 1/2H_2O$. Calc'd : C, 39.39; H, 3.31; N, 5.38; S, 23.37. Found : C, 39.65; H, 2.98; N, 5.11; S, 22.96.

The title compound as a mixture of cis and trans isomers is prepared in 50% yield by the same procedure and in the same molar amounts as described in Example 1 from 1-(benzylthio)-2-nitroethenethiol potassium salt, nmr (DMSO-$D_6$) 2.04 (s, 3), 3.58 (broad s, 2) 4.03 and 4.11 (two s, 2), 4.42 and 4.50 (two s, 2) 4.89 (q, 2), 5.1 (two d, 1), 5.7 (m, 1), 7.42 (s, 5), 7.50 (s, 1).

Elemental Analysis for $C_{21}H_{21}N_3O_8S_2 \cdot 1/2H_2O$: Calc'd : C, 45.97; H, 4.04; N, 7.55. Found : C, 46.26; H, 4.25; N, 7.66.

| BA SU | 6633 | .031 |
|---|---|---|
| ST AU | 6538P | .122 |
| " | Smith | .122 |
| " | CHP | .488 |
| " | 53–180 | .488 |
| NE CA | 8193 | 7.81 |
| SA PA | 11737 | 62.5 |
| KL PN | 10031 | 125 |
| BO BR | 4617 | 250 |
| PR VU | 6896 | 125 |
| ES CO | 9637 | 250 |

EXAMPLE 10

7-[2-[(cyanoimino)(phenylmethylthio)methylthio]acetamido]cephalosporanic acid

The title compound is prepared in 53% yield by the same procedure and in the same molar amounts as described in Example 1 from potassium benzyl cyanoimidodithiocarbonate (produced by the method of Timmons, U.S. Pat. No. 3,658,901), nmr (DMSO-$D_6$) 2.05 (s, 3), 3.6 (broad s, 2), 4.20 (s, 2), 4.62 (s, 2), 4.9 (q, 2), 5.13 (d, 1), 5.64 (d, 1) 7.40 (s, 5).

Elemental Analysis for $C_{21}H_{20}N_4S_3O_6 \cdot 2\ 1/2H_2O$: Calc'd: C, 44.59; H, 4.46; N, 9.90. Found : C, 44.08; H, 3.80; N, 9.70.

The potassium salt of the title compound is prepared in quantitative yield by the same procedure as described in Example 6 from the product of Example 10.

Elemental Analysis for $C_{21}H_{19}KN_4O_6S_3 \cdot 2H_2O$: Calc'd C, 42.40; H, 3.90; N, 9.42. Found : C, 42.22; H, 3.94; N, 8.85.

| ES CO | 9637 | 15.6 |
|---|---|---|
| NE CA | 8193 | 62.5 |
| SA PA | 11737 | 3.90 |
| KL PN | 10031 | 15.6 |
| BO BR | 4617 | 15.6 |
| PR VU | 6896 | 15.6 |
| ES CO | 920 | 62.5 |
| BA SU | 6633 | .122 |
| ST AU | 6538P | .976 |
| ST AU | Smith | .976 |
| ST AU | CHP | 3.90 |
| ST AU | 53–180 | 1.95 |

EXAMPLE 11

7-[2-(2-Cyano-1-cyanomethylthio-2-methylsulfonylethenylthio)acetamido]cephalosporanic acid Following the procedure presented in the first paragraph of Example 1, 3,3-dimercapto-2-methylsulfonyl-2-propenenitrile dipotassium salt is prepared, m.p. 270°–271°C., (decomp.) nmr (DMSO-$D_6$) 3.30 (s, 3).

Elemental Analysis for $C_4H_3K_2NO_2S_3$: Calc'd: C, 17.69; H, 1.11; N, 5.16; Found : C, 18.08; H, 1.28; N, 5.26;

Following the procedure presented in the latter part of the first paragraph of Example 1, 3-cyanomethylthio-3-mercapto-2-methylsulfonyl-2-propanenitrile potassium salt is prepared. Following the procedure disclosed in the second paragraph of Example 1 the title compound is prepared in 20% yield from 3-cyanomethylthio-3-mercapto-2-methylsulfonyl-2-propenenitrile potassium salt nmr (DMSO-$D_6$) 2.05 (s, 3), 3.30 (s, 3), 3.65 (broad s, 2) 4.1–4.2 (m, 4), 4.95 (q, 2) 5.33 (d 1), 5.8 (m, 1).

Elemental Analysis for $C_{16}H_{17}KN_4O_8S_4 \cdot H_2O$: Calc'd: C, 33.20; H, 3.08; N, 9.68. Found: C, 33.47; H, 3.31; N, 9.19.

| BA SU | 6633 | 15.6 |
| ST AU | 6538P | 250 |
| ST AU | Smith | 250 |

EXAMPLE 12

7-[2-[(cyanoimino)(2-ethoxy-2-oxoethylthio)methyl-thio]acetamido]cephalosporanic acid The title compound is prepared in 54% yield by the same procedure and in the same molar amounts as described in Example 1 from potassium ethoxycarbonylmethyl cyanoimidodithiocarbonate (produced by the method of Timmons, U.S. Pat. No. 3,658,901), nmr (DMSO-D$_6$) 1.28 ($t$, 3), 2.08 ($s$, 3) 3.65 (broad $s$, 2), 4.15 ($q$, 2) 4.27 (broad $s$, 4), 4.95 ($q$, 2), 5.15 ($d$, 1), 5.7 ($m$, 1).

Elemental Analysis for $C_{18}H_{20}N_4S_3O_8$: Calc'd: C, 41.85; H, 3.90; N, 10.85. Found: C, 41.08; H, 4.19; N, 10.87.

The potassium salt of the title compound is prepared in 61% yield by the same procedure as described in Example 6 from the product of Example 12

Elemental Analysis for $C_{18}H_{19}N_4S_3O_8K \cdot 1/2H_2O$: Calc'd: C, 38.35; 3.58; 9.94. Found: C, 38.38; 3.26; 9.62.

| BA SU | 6633 | .122 |
| ST AU | 6538P | .976 |
| ST AU | Smith | .488 |
| ST AU | CHP | 3.90 |
| ST AU | 53–180 | 1.95 |
| NE CA | 8193 | 62.5 |
| ES CO | 9637 | 250 |
| SA PA | 11737 | 31.3 |
| KL PN | 10031 | 31.3 |
| BO BR | 4617 | 250 |
| PR VU | 6896 | 62.5 |
| ES CO | 920 | 250 |

EXAMPLE 13

7-[2-[(cyanoimino)(4-nitrophenylmethylthio)methyl-thio]acetamido]cephalosporanic acid The title compound is prepared is 35% yield by the same procedure and in the same molar amounts as described in Example 1 from potassium p-nitrobenzyl cyanoimidodithiocarbonate (produced by the method of Timmons, U.S. Pat. No. 3,658,901), nmr (DMSO-D$_6$) 2.07 ($s$, 3), 3.5 (broad $m$, 2), 4.21 ($s$, 2), 4.72 ($s$, 2) 15.01 ($q$, 2), 5.13 ($d$, 1), 5.7 ($m$, 1), 7.95 ($q$, 4)

Elemental Analysis for $C_{21}H_{19}N_5S_3O_8$ : Calc'd: C, 44.95; H, 3.39; N, 12.38. Found: C, 44.92; H, 3.68; N, 11.63.

The potassium salt of the title compound is prepared in 95% yield by the same procedure as described in Example 6 from the product of Example 13.

Elemental Analysis for $C_{21}H_{18}N_5S_3KO_8 \cdot 1/2H_2O$: Calc'd: C, 41.15; H, 3.00; N, 11.43. Found: C, 41.18; H, 3.49; N, 11.10.

| BA SU | 6633 | .488 |
| ST AU | 6538P | 1.95 |
| ST AU | Smith | 1.95 |

-continued

| ST AU | CHP | 3.90 |
| SU AU | 53–180 | 3.90 |
| NE CA | 8193 | 62.5 |
| ES CO | 9637 | 250 |
| SA PA | 11737 | 62.5 |
| KL PN | 10031 | 250 |
| BO BR | 4617 | 125 |
| PR VU | 6896 | 62.5 |

EXAMPLE 14

7-[2-[(cyanomethylthio)(methylsulfonylimino)me-thylthio]acetamido]cephalosporanic acid Following the procedure presented in the first paragraph of Example 6, methylsulfonylcarbonimidodithioic acid cyanomethyl ester potassium salt is prepared from (methylsulfonyl) carbonimidodithioic acid dipotassium salt. nmr (DMSO-D$_6$) 3.08 ($s$, 3), 3.90 ($s$, 2).

Elemental Analysis for $C_4H_5KN_2O_2S_3$: Calc'd: C, 19.34; H, 2.02; N, 11.28. Found: C, 20.22; H, 2.03; N, 10.95.

The title compound is prepared in 48% yield, by the same procedure and in the same molar amounts as described in Example 1 from the product of the preceding paragraph, nmr (DMSO-D$_6$) 2.03 ($s$, 3), 3.22 ($s$, 3), 3.59 ($s$, 2), 4.20 ($s$, 2), 4.40 ($s$, 2), 4.89 ($q$, 2), 5.13 ($d$, 1), 5.76 ($d$, 1).

Elemental Analysis for $C_{16}H_{18}N_4O_8S_4$: Calc'd: C, 36.77; H, 3.47; N, 10.72. Found: C, 36.77; H, 3.23; N, 10.15.

The potassium salt of the title compound is prepared in 85% yield by the same procedure as described in Example 6 from the product of Example 14

Elemental Analysis for $C_{16}H_{17}KN_4O_8S_4 \cdot H_2O$: Calc'd: C, 33.20; H, 3.08; N, 9.68. Found: C, 33.47; H, 3.31; N, 9.19.

| BA SU | 6633 | .244 |
| ST AU | 6538P | 1.95 |
| ST AU | Smith | 1.95 |
| ST AU | CHP | 7.81 |
| ST AU | 53–180 | 7.81 |
| NE CA | 8193 | 125 |
| PS AE | 10145 | 125 |
| ES CO | 9637 | 125 |
| SA PA | 11737 | 15.6 |
| DL PN | 10031 | 31.3 |
| BO BR | 4617 | 62.5 |
| PR VU | 6896 | 31.3 |
| HE SP | 9955 | 250 |
| ES CO | 920 | 125 |

EXAMPLE 15

7-[2-[(cyanoimino)(2-hydroxy-2-oxoethylthio)me-thylthio]acetamido]cephalosporanic acid Following the procedure presented in the first paragraph of Example 6, cyanocarbonimidodithioic acid carboxymethyl ester dipotassium salt, potassium bromide is prepared in 98% yield from cyanoimidodithiocarbonate dipotassium salt.

Elemental Analysis for $C_4H_2K_2N_2O_2S_2 \cdot KBr$ : Calc'd: C, 12.93; H, 0.54; N, 7.54. Found : C, 12.67; H, 0.48; N, 7.13.

The title compound is prepared in 25% yield by the same procedure and in the same molar amounts as described in Example 1 from cyanocarbonimidodithioic acid carboxymethyl ester dipotassium salt, potassium bromide, nmr (DMSO-D$_6$) 2.05 (s, 3), 3.52 (broad s, 2), 4.2 (m, 4), 4.9 (q, 2), 5.2 (d, 1), 5.7 (d, 1).

Elemental Analysis for C$_{16}$H$_{16}$N$_4$O$_6$S$_3$.H$_2$O: Calc'd : C, 37.93; H, 3.58; N, 11.06. Found : C, 38.40; H, 3.80; N, 10.82.

| BA SU | 6633  | 1.95 |
|-------|-------|------|
| ST AU | 6538P | 15.6 |
| ST AU | Smith | 7.81 |
| ST AU | CHP   | 62.5 |
| SA PA | 11737 | 125  |
| KL PN | 10031 | 250  |
| PR VU | 6896  | 125  |

EXAMPLE 16

7-[2-[(3-chlorophenylmethylthio)(cyanoimino)methylthio]acetamido]cephalosporanic acid Following the procedure presented in the first paragraph of Example 6, cyanocarbonimidodithioic acid 3-chlorobenzyl ester potassium salt is prepared in 92% yield from cyanoimidodithiocarbonate dipotassium salt, nmr (DMSO-D$_6$) 4.20 (s,2), 7.2–7.5 (m, 4).

Elemental Analysis for C$_9$H$_6$ClK N$_2$S$_2$.H$_2$O : Calc'd : C, 37.29; H, 2.43; N, 9.67. Found : C, 37.15; H, 2.16; N, 9.90.

The title compound is prepared in 59% yield by the same procedure and in the molar amounts as described in Example 1 from cyanoimidodithioic acid 3-chlorobenzyl ester potassium salt, nmr (DMSO-D$_6$) 2.02 (s, 3), 3.56 (broad s, 2) 4.18 (s, 2), 4.58 (s, 2), 4.86 (q, 2), 5.08 (d,1), 5.67 (d, 1), 7.5 (m, 4).

Elemental Analysis for C$_{21}$H$_{19}$ClN$_4$S$_3$O$_6$.2H$_2$O : Calc'd: C, 42.67; H, 3.92; N, 9.48. Found : C, 42.89; H, 3.45; N, 9.76.

The potassium salt of the title compound is prepared in 91% yield by the same procedure as described in Example 6 from the product of Example 16.

Elemental Analysis for C$_{21}$H$_{18}$ClKN$_4$O$_6$S$_3$.1/2H$_2$O : Calc'd: C, 41.88; H, 3.18; N, 9.30. Found : C, 41.60; H, 3.23; N, 9.03.

| BA SU | 6633   | .122 |
|-------|--------|------|
| ST AU | 6538P  | .976 |
| ST AU | Smith  | 1.95 |
| ST AU | CHP    | 1.95 |
| ST AU | 53-180 | 3.90 |
| NE CA | 8193   | 125  |
| ES CO | 9637   | 250  |
| SA PA | 11737  | 31.3 |
| KL PN | 10031  | 125  |
| BO BR | 4617   | 250  |
| PR VU | 6896   | 125  |
| ES CO | 920    | 250  |

EXAMPLE 17

7-[2-[(cyanoimino)(2-propynylthio)methylthio]acetamido]cephalosporanic acid

Following the procedure presented in the first paragraph of Example 6, cyanocarbonimidodithioic acid 2-propynyl ester, potassium salt is prepared in 35% yield from cyanoimidodithiocarbonate dipotassium salt and propargyl chloride.

Elemental Analysis for C$_5$H$_3$KN$_2$S$_2$.3/4H$_2$O : Calc'd: C, 28.89; H, 2.18; N, 13.48. Found : C, 28.64; H, 1.63; N, 13.60.

The title compound is prepared in 50% yield by the same procedure and in the same molar amounts as described in Example 1 from cyanocarbonimidodithioic acid 2-propynyl ester, potassium salt, nmr (DMSO-D$_6$) 2.05 (s,3), 3.3 (m, 1), 3.6 (broad s, 2), 4.2 (broad s, 4), 4.85 (q, 2) 5.11 (d, 1), 5.7 (m, 1).

Elemental Analysis for C$_{17}$H$_{16}$N$_4$O$_6$S$_3$.2H$_2$O : Calc'd: C, 40.47; H, 4.00; N, 11.10. Found : C, 40.55, H; 3.45; N, 10.91.

The potassium salt of the title compound is prepared 95% yield by the same procedure as described in Example 6 from the product of Example 17.

Elemental Analysis for C$_{17}$H$_{15}$KN$_4$O$_6$S$_3$.2H$_2$O : Calc'd: C, 37.62; H, 3.53; N, 10.33. Found : C, 37.56; H, 3.02; N, 10.02.

| BA SU | 6633   | .122 |
|-------|--------|------|
| ST AU | 6538P  | .488 |
| ST AU | Smith  | .488 |
| ST AU | CHP    | 3.90 |
| ST AU | 53-180 | 3.90 |
| NE CA | 8193   | 125  |
| ES CO | 9637   | 31.3 |
| SA PA | 11737  | 7.81 |
| KL PN | 10031  | 7.81 |
| PR VU | 6896   | 62.5 |
| ES CO | 920    | 62.5 |

EXAMPLE 18

7-[2-[(4-Chlorophenylmethylthio)(cyanoimino)methylthio]acetamido]cephalosporanic acid Following the procedure presented in the first paragraph of Example 6, cyanocarbonimidodithioic acid 4-chlorobenzyl ester, potassium salt is prepared in 95% yield from cyanoimidodithiocarbonate dipotassium salt and nmr (DMSO-D$_6$) 4.18 (s, 2) 7.36 (m, 4).

Elemental Analysis for C$_9$H$_6$ClKN$_2$S$_2$.1/2H$_2$O Calc'd: C, 37.29; H, 2.43; N, 9.67. Found : C, 37.54; H, 2.31; N, 9.67.

The title compound is prepared in 52% yield by the same procedure and in the same molar amounts as described in Example 1, from cyanocarbonimidodithioic acid 4-chlorobenzylester, potassium salt, nmr (DMSO-D$_6$) 2.04 (s, 3) 3.6 (broad s, 2), 4.19 (s, 2), 4.59 (s, 2), 4.87 (q, 2), 5.13 (d, 1), 5.70 (d, 1), 7.46 (s, 4).

Elemental Analysis for C$_{21}$H$_{19}$ClN$_4$O$_6$S$_3$.H$_2$O : Calc'd : C, 44.01; H, 3.69; N, 9.78. Found : C, 44.17; H, 3.48; N, 9.78.

| BA SU | 6633   | .488 |
|-------|--------|------|
| ST AU | 6538P  | 1.95 |
| ST AU | Smith  | 1.95 |
| ST AU | CHP    | 7.81 |
| ST AU | 53-180 | 3.90 |
| NE CA | 8193   | 250  |
| ES CO | 9637   | 250  |
| SA PA | 11737  | 31.3 |
| KL PN | 10031  | 125  |
| BO BR | 4617   | 125  |
| PR VU | 6896   | 62.5 |
| ES CO | 920    | 250  |

EXAMPLE 19

7-[2-[(cyanoimino)(2-propenylthio)methylthio]acetamido]cephalosporanic acid

The title compound is prepared in 74% yield by the same procedure and in the same molar amounts as described in Example 1 from potassium allyl cyanoimidodithiocarbonate (produced by the method of Timmons, U.S. Pat. No. 3,658,901), nmr (DMSO-$D_6$) 2.02 ($s$, 3), 3.57 (broad $s$, 2), 3.98 ($d$, 2) 4.17 ($s$, 2), 4.9 ($q$, 2), 5–6 ($m$, 4).

Elemental Analysis for $C_{17}H_{18}N_4O_6S_3 \cdot 1/2H_2O$ : Calc'd: C, 42.58; H, 3.99; N, 11.67. Found : C, 42.73; H, 3.97; N, 11.67.

The potassium salt of the title compound is prepared in quantitative yield by the same procedure as described in Example 6 from the product of Example 19.

Elemental Analysis for $C_{17}H_{17}KN_4O_6S_3 \cdot H_2O$ : Calc'd: C, 38.76; H, 3.64; N, 10.64. Found : C, 38.47; H, 3.27; N, 10.74.

| | | |
|---|---|---|
| BA SU | 6633 | .488 |
| ST AU | 6538P | 1.95 |
| ST AU | Smith | 1.95 |
| ST AU | CHP | 7.81 |
| ST AU | 53–180 | 3.90 |
| NE CA | 8193 | 250 |
| ES CO | 9637 | 250 |
| SA PA | 11737 | 31.3 |
| KL PN | 10031 | 125 |
| BO BR | 4617 | 125 |
| PR VU | 6896 | 31.3 |
| ES CO | 920 | 250 |

What is claimed is:

1. A compound which is 7-[2-[(cyanomethylthio)(methylsulfonylimino)methylthio]acetamido]cephalosporanic acid or an alkali metal, alkaline earth metal or ammonium salt thereof.

* * * * *